(12) United States Patent
Larkin

(10) Patent No.: US 7,806,882 B1
(45) Date of Patent: Oct. 5, 2010

(54) TAMPON SATURATION MONITORING SYSTEM

(76) Inventor: Kevin B. Larkin, 1140 Porque La., Pebble Beach, CA (US) 93953

( * ) Notice: Subject to any disclaimer, the term of this patent is extended or adjusted under 35 U.S.C. 154(b) by 745 days.

(21) Appl. No.: 11/673,373

(22) Filed: Feb. 9, 2007

(51) Int. Cl.
*A61F 13/15* (2006.01)
*A61F 13/20* (2006.01)

(52) U.S. Cl. ............... 604/385.18; 604/385.17; 604/361

(58) Field of Classification Search ........... 604/385.17, 604/385.18, 904
See application file for complete search history.

(56) References Cited

U.S. PATENT DOCUMENTS

| 3,794,024 | A | 2/1974 | Kokx | |
|---|---|---|---|---|
| 5,903,222 | A | 5/1999 | Kawarizadeh | |
| 5,904,671 | A | 5/1999 | Navot | |
| 6,348,640 | B1 * | 2/2002 | Navot et al. | 604/361 |
| 6,506,958 | B2 | 1/2003 | Williams | |
| 6,560,787 | B2 | 5/2003 | Mendoza | |
| 6,817,039 | B1 | 11/2004 | Grilliot | |
| 6,896,653 | B1 * | 5/2005 | Vail et al. | 600/135 |
| 6,972,010 | B2 | 12/2005 | Pesce | |
| 2004/0095247 | A1 | 5/2004 | De Haan | |
| 2005/0137530 | A1 * | 6/2005 | Campbell et al. | 604/131 |
| 2008/0125700 | A1 * | 5/2008 | Moberg et al. | 604/67 |
| 2008/0125701 | A1 * | 5/2008 | Moberg et al. | 604/67 |

* cited by examiner

*Primary Examiner*—Melanie J Hand
(74) *Attorney, Agent, or Firm*—Johannes Schneeberger

(57) ABSTRACT

A tampon that has a sensor and a signal line that peripherally connects the sensor with a peripheral signal processor. The sensor provides a blood wetting signal in response to a progressing blood saturation boundary in the tampon. The signal may be resistive, capacitive or optic. The simple sensor has two proximal signal terminals separated by a fluid responsive medium in wetting communication with the tampon's body. The tampon may be removed by use of the signal line. From signal timing and/or signal gradient the processor may predict when the tampon needs to be changed.

20 Claims, 8 Drawing Sheets

# TAMPON SATURATION MONITORING SYSTEM

FIELD OF INVENTION

The present invention relates to systems and devices for monitoring the menstrual blood saturation progress in vaginally inserted tampons.

BACKGROUND OF INVENTION

Tampons are conveniently used by women to absorb menstrual blood. For that purpose a tampon is commonly vaginally inserted. The tampon acts as a fluid absorption body that seals the vaginal channel and at the same time absorbs menstrual blood from the uterus until the tampon reaches its fluid absorption limit. If the tampon is not replaced at that time, menstrual blood may leak out of the tampon.

For a woman it may be difficult to predict when the tampon has reached its fluid absorption limit. Therefore, there exists a need for a system for monitoring the saturation progress of a vaginally inserted tampon. The present invention addresses this need.

During the menstrual period a large number of tampons may be needed and replaced in short time intervals. Therefore, there exists a need for a tampon saturation monitoring system that utilizes simple and inexpensive yet reliable sensor configurations. The present invention also addresses this need.

There exists also a need for a tampon user to receive a preemptive forecast when a tampon in use may reach its fluid saturation limit. The present invention also addresses this need.

SUMMARY OF INVENTION

A tampon saturation monitoring system of the present invention features a tampon that has a saturation sensor positioned inside the fluid absorption body and a first signal line that peripherally connects the saturation sensor with a peripheral signal processor. The fluid saturation sensor provides a wetting response signal in conjunction with a blood saturation boundary that is axially progressing along the fluid absorption body.

The saturation sensor is a simple device including at least two proximal signal terminals separated by a fluid responsive medium that is preferably made of the same gauze material as the fluid absorption body is fabricated from. The two proximal signal terminals have a signal potential across the fluid responsive medium, which is in wetting communication with the fluid absorption body. The saturation sensor may be configured to provide a resistive, capacitive or optic wetting response signal, which the processor analyzes to derive information of the saturation boundary progress of the fluid absorption body. The processed saturation information is passed on to a saturation notifier, which may be a buzzer, a tactile notifier in skin contact or a software application installed on a portable multifunction device.

The processor may also compute from signal timing and/or signal gradient a forecast of the moment when the tampon will reach its full saturation. In that way, a tampon user may conveniently plan ahead to timely replace the inserted tampon.

The first signal line may be a cable that is structurally combined with the fluid absorption body such that the tampon may be pulled from its vaginally inserted position by use of the cable. The cable may feature a connector to easily connect and/or disconnect to the processor. The processor may be configured as a disposable device with a battery life corresponding to a predetermined number of tampons and this processor may be packaged together in each box of tampons. The processor may also be configured as a standalone unit with a replaceable battery.

DETAILED DESCRIPTION

Figure 1:
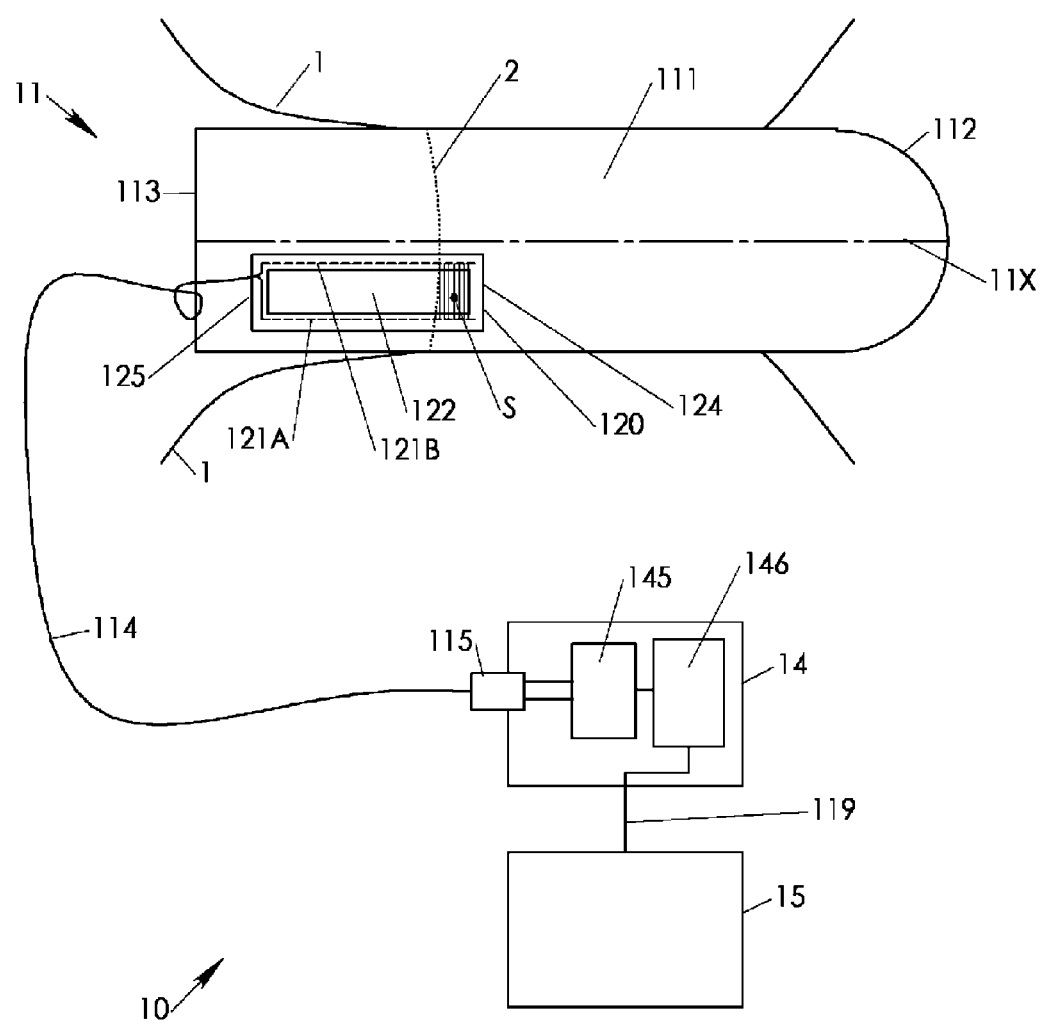
FIG. 1 is a schematic view of a first embodiment of the invention in vaginally inserted position.

Referring to FIGS. 1-4, a tampon saturation monitoring system 10 includes a tampon 11, a signal processor 14 and a notifier 15. The tampon 11 has a well known fluid absorption body 111 as commonly used in commercially available tampons, a saturation sensor 120 and a first signal line 114, which is preferably a cable. The fluid absorption body 111 extends along a saturation progress axis 11X. The fluid absorption body 111 has a fluid access end 112 and a peripheral end 113 opposite to the fluid access end 112 in the direction of the saturation progress axis 11X. When the tampon 11 is positioned in the vaginal channel 1, menstrual blood from the uterus is mainly absorbed by the fluid absorption body 111 in the vicinity of the fluid access end 112 and axially progresses substantially in a direction along the saturation progress axis 11X. The more blood is absorbed, the further the blood saturation boundary 2 progresses towards the peripheral end 113.

Should the blood saturation boundary 2 reach the peripheral end 113, blood may seep out of the tampon 11 as may be well appreciated by anyone skilled in the art. To prevent this from happening and to give the tampon 11 user sufficiently early warning, the saturation sensor 120 is positioned axially with respect to the saturation progress axis 11X generally in between the fluid access end 112 and the peripheral end 113, preferably in close proximity to the peripheral end 113. The saturation sensor 120 preferably includes two proximal signal terminals 121A, 121B having a signal potential across a fluid responsive medium 122 that separates the signal terminals 121A, 121B.

The fluid responsive medium 122 is in a wetting communication with the fluid absorption body 111. This means that as the saturation boundary 2 axially progresses past the saturation sensor 120, the menstrual blood following the saturation boundary 2 is wetting the fluid responsive medium 122.

As the saturation boundary 2 penetrates the fluid responsive medium 122, a wetting response signal S is generated in conjunction with the axially progressing saturation boundary 2. The wetting response signal is generated when the signal potential between the two proximal signal terminals 121A, 121B is activated by a change of physical properties in the fluid responsive medium 122 due to the wetting. The physical properties change may include a change of electric resistance, dimensional spacing, light attenuation, and/or light filtering as explained in more detail in the below.

In a particular case in which the saturation sensor 120 extends substantially axially along the saturation progress axis 11X as depicted in the FIGS. 1-5, the wetting communication may be radially and axially responsive to the saturation boundary 2 while progressing in between the frontal end 124 and the rear end 125 of the saturation sensor 120. In that case, the wetting response signal S may be gradual and in a proportion to the axially progressing saturation boundary 2 in the radial vicinity of the saturation sensor 120 in between its frontal end rear ends 124, 125. From the gradual wetting response signal S, the processor 14, and/or the notifier 15 may provide a tampon 11 full forecast, which may include a time span until the tampon 11 reaches its fluid absorption limit and optionally an forecast error margin. A forecast error margin may consider fluctuations in the axial progression of the saturation boundary 2 as may well occur due to a varying level menstrual bleeding.

In embodiments in which the wetting response signal S is a resistive signal occurring between two proximal signal terminals 121A, 121B configured as electrical conductors, any stray current flow from the proximal signal terminals 121A, 121B to the vaginal lining 1 may need to be kept below a well established body leakage current maximum as is well known to anyone skilled in the art. According to the well known Ohm's law, a current flow for a given conductivity is proportional to the voltage difference along the conductive path. Hence, the voltage difference between the proximal signal terminals 121A, 121B may be selected sufficiently low and independently of a processing voltage of the processor 14. The processing voltage may be a voltage required by the logic circuitry inside the processor 14. The voltage difference between the signal terminals 121A, 121B may be a fraction of the processing voltage and selected in conjunction with a predetermined conductivity between at least one of the signal terminals 121A, 121B and the proximal vaginal lining 1 and the maximum allowed body leakage current. At the time the invention was made, the maximum allowed body leakage current known to the inventor is 10 microampere. The processor 14 may feature a processing circuitry 146 that operates at the processing voltage and a low voltage circuitry 145 that provides the voltage difference at a fraction of the processing voltage.

The present invention includes embodiments with more than two signal terminals 121A, 121B which may be radially spread across a cross section of the tampon 11 to capture eventual axial progress fluctuations of the saturation boundary 2. In such a case, the wetting response signal S may be summed and averaged by the processor 14 and/or balanced within the saturation sensor 120 by grouping and conductively connecting the number of proximal signal terminals 121A, 121B in two sets.

The first signal line 114 peripherally connects the saturation sensor 120 across the peripheral end 113 with the signal processor 14 preferably via a connector 115. The signal processor 14 computes the progress of the saturation boundary 2 from the wetting response signal S. The notifier 15, which is in communication with the signal processor 14 notifies the tampon user about the progress of the saturation boundary 2.

In a first embodiment of the invention, the at least two proximal signal terminals 121A, 121B are electric conductors. The physical property change of the fluid responsive medium 122 due to menstrual blood wetting may be an electric resistance change. The wetting response signal S may occur in between the electric conductors 121A, 121B and across the fluid responsive medium 122 in conjunction with electric resistance change and a voltage difference between the two electric conductors 121A, 121B. The voltage difference may be applied by the processor 14 via the connector 115 and the cable 114.

Figure 2:
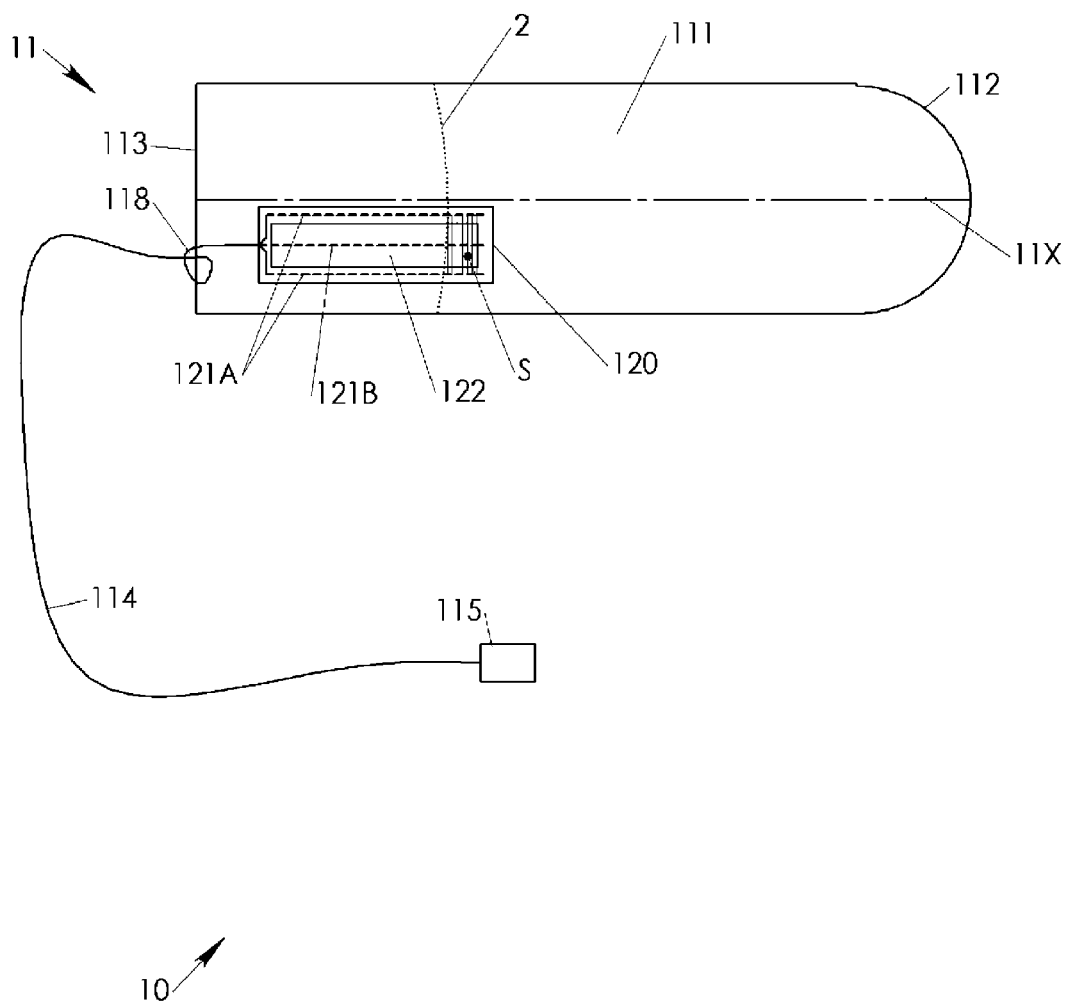
FIG. 2 is a schematic view of a tampon with a saturation sensor according to a second embodiment of the invention.

The electric resistance change may result from the menstrual blood that is wetting the fluid responsive medium 122. Blood has a well known conductivity due to its iron content as is well known in the art. The fluid responsive medium 122 may be configured with a dry conductivity that substantially differs from the blood's conductivity to provide the electric resistance change in conjunction with its blood wetting. As depicted in FIG. 2, one of the electric conductors 121A may be an enveloping conductor 121A encapsulating the second electric conductor 121B and acting as an electric ground. As a result, eventual electric current flow due the electric resistance change may be contained within the enveloping conductor 121A irrespective of an eventual outside conductive path of the absorbed blood outside the saturation sensor 120. The outside conductive path may be related to the wetting communication of the fluid responsive medium 122 with the fluid absorption body 111.

The wetting communication across the enveloping conductor 121A may be implemented by configuring the enveloping conductor as a fluid permeable material such a metal mesh, metal weaving and/or perforated metal foil. In case of a coaxial cable employed as the first signal line 114, the enveloping conductor 121A may be an integral conductive part of the coaxial cable's 114 shielding mesh. A shielding mesh may be the well known part of a coaxial cable 114 circumferentially protruding along the cable 114 to electrically and/or magnetically shield core wires against the surrounding environment as is well known in the art.

The first signal line 114 is preferably a cable 114 such as an optic fiber cable or an electric cable such as an unshielded strand cable or a coaxial cable as described above. The cable 114 may be structurally combined with the fluid absorption body 111 such that the tampon 11 may be pulled out of its vaginally inserted position 1 via said cable 114. In the preferred case in which the fluid absorption body 111 is made of rolled up gauze as is well known in the art, the cable 114 may be knotted with the gauze at the peripheral end 113. In that way, tensile stress during the removal of the tampon 11 is conveniently transferred from the cable 114 onto the fluid absorption body 111 via the knot 118. At the same time, the knot 118 may serve to transfer eventual cable 114 stress during tampon 11 use onto the fluid absorption body 111 such that the saturation sensor 120 remains free of cable 114 stress at a constant position within the fluid absorption body 111. The constant position may assist in providing a more accurate tampon full forecast.

Figure 5:
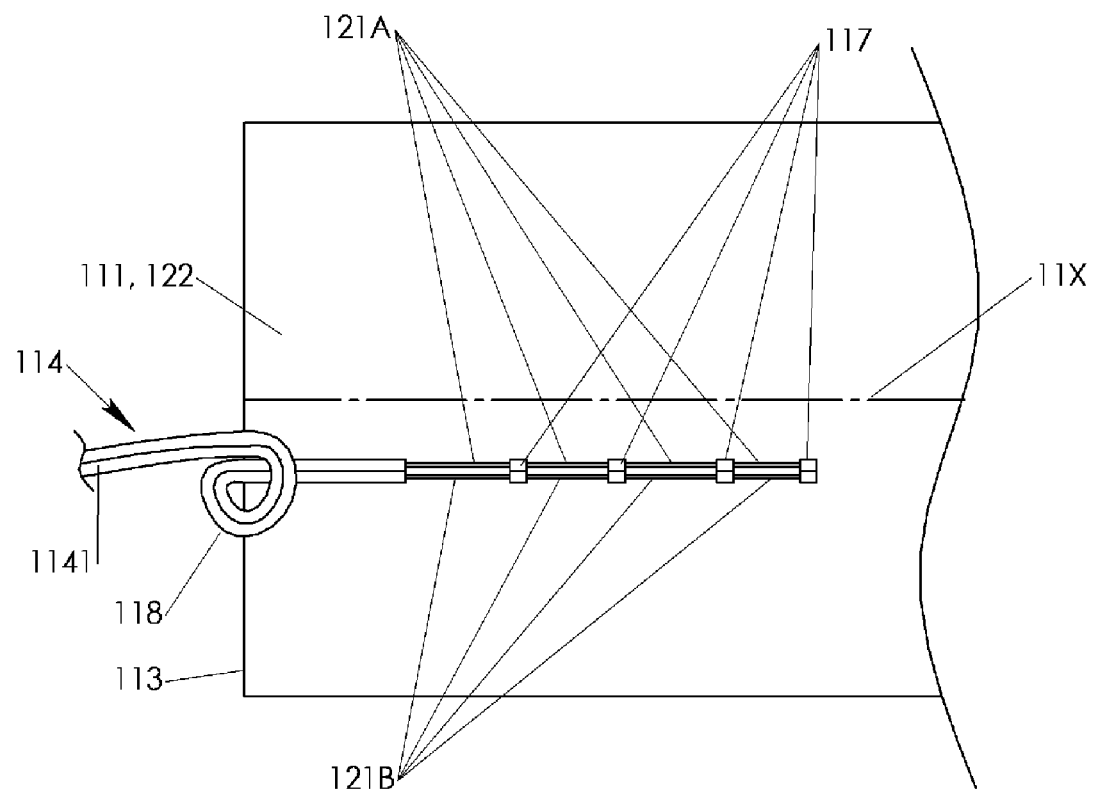
FIG. 5 is a schematic partial view of a tampon of the present invention.

At least one of the proximal signal terminals 121A, 121B may be integral part of a strand of the cable 114. In case of an optic cable 114, the strand may be an optic fiber. In case of an electric cable 114, the strand may be an electric wire strand or as described above a shielding mesh. As depicted in FIG. 5, the strands of the proximal signal terminals 121A, 121B may be separated and spaced from each other by a number of spacers 117 that are axially arrayed with respect to the saturation progress axis 11X. The cable 114 may feature a well known surrounding insulation 1141 and the spacer(s) 117 may be of that surrounding insulation 117. In that way, the saturation sensor 120 may be simply fabricated from the cable 114 by separating a number of spacers 117 from the surrounding insulation 1141 in such a way that their encapsulating structural integrity remains intact. The cable 114 strands may be exposed to the fluid responsive medium 122, by sliding the separated spacers 117 along the strands. In that way constant spacing between the proximal signal terminals 121A, 121B is achieved in a simple fashion during fabrication.

The fluid responsive medium 122 may be integral part of the fluid absorption body 111. In the preferred case of the fluid absorption body 111 being made of a well known gauze material, the saturation sensor 120 may be fabricated by interweaving separated proximal signal terminals 121A, 121B with the gauze material and/or rolling them up together with gauze material such that the proximal signal terminals 121A, 121B are preferably at a central location of the fully fabricated tampon 11. The knot 118 may be fabricated prior to rolling up the gauze material.

Figure 6:
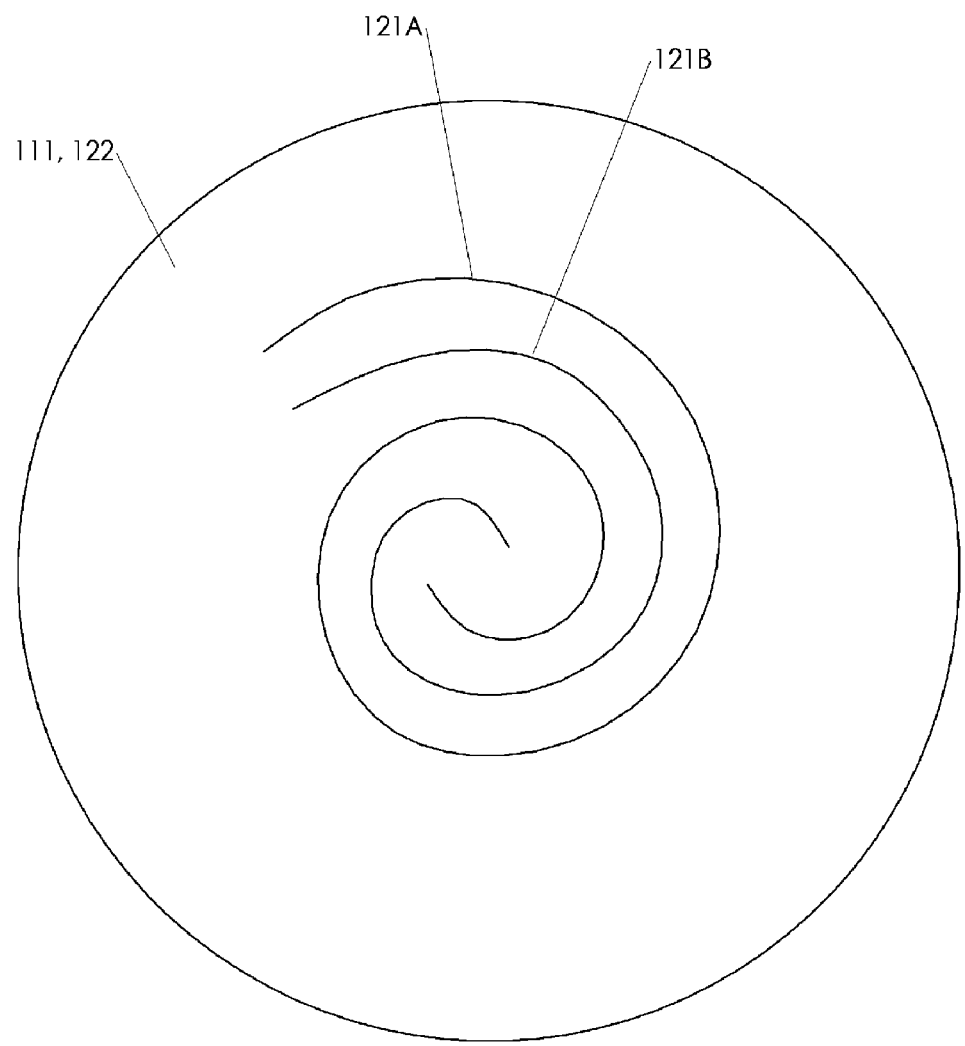
FIG. 6 is a schematic cross section view of a tampon including a saturation sensor capacitor.

Referring to FIG. 6, the proximal signal terminals 121A, 121B and the fluid responsive medium 122 may together a capacitor. The wetting response signal S may be an electric capacitance change of the saturation sensor 120. The electric capacitance change may result from a wetted swelling of the fluid responsive medium. The wetted swelling may occur as the fluid responsive medium absorbs menstrual blood. The wetted swelling may push the proximal signal terminals 121A, 121B further apart, which reduces the capacitance between the proximal signal terminals 121A, 121B according to the well known principles of an electric capacitor. The proximal signal terminals 121A, 121B may be interweaved rolled up, perforated, metal foils separated by the fluid responsive medium 122. The metal foils 121A, 121B perforation may provide for the wetting communication across metal foils 121A, 121B. The fluid responsive medium 122 may again be from the same gauze material as the fluid absorption body 111. The perforated metal foils 121A, 121B may be rolled up together with the fluid absorption body 111, making the tampon 11 fabrication very simple and inexpensive. In addition, the metal foils 121A may feature an insulating coating such that no electric current flow will occur inside the fluid absorption body 111 irrespective of the eventual presence of conductive blood.

Figure 3:
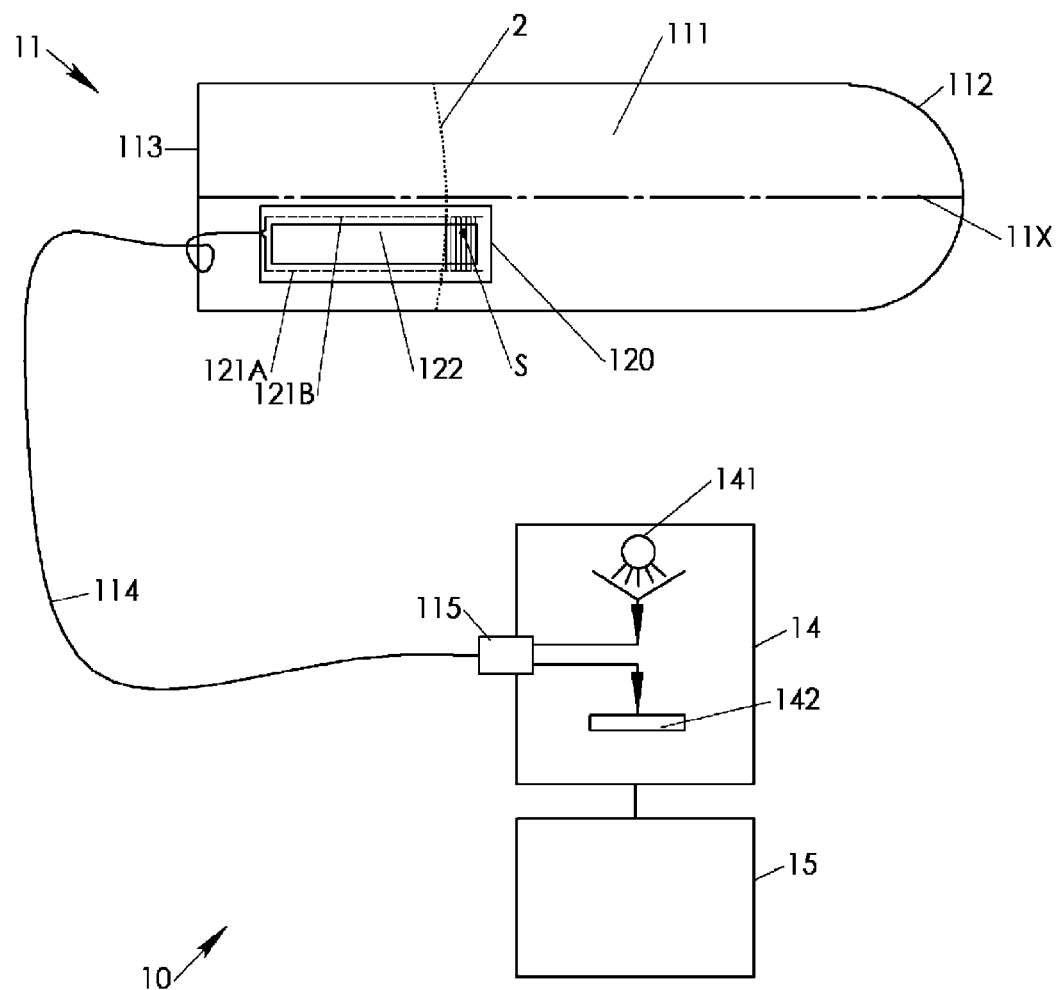
FIG. 3 is a schematic view of a third embodiment of the invention.

Referring to FIG. 3, the saturation sensor 120 may be an optical bridge featuring a light emitter 121A proximal to a light receiver 121B. The separating fluid responsive medium 122 may be optically responsive. The wetting response signal S may be a light attenuation change and/or a light spectrum change of the fluid responsive medium 122 in response to the blood wetting of the fluid responsive medium 122. At least one but preferably both light emitter 121A and light receiver 121B may be integral optic fiber strands of the cable 114 extending into the saturation sensor 120. The fluid responsive medium 122 may be of a gauze material of a thickness and optic permeability suitable for attaining the desired optic responsiveness as may be well appreciated by anyone skilled in the art.

The processor 14 may feature a light source 141 and a light sensor 142 optically connected to the cable 114 via connector 115. The light source 141 pumps light across the connector 115 and through the cable 114 into the fiber end 121A, which may be stripped off its reflective coating and/or otherwise processed in a well known fashion such that the light may emerge laterally from the exposed fiber end 121A. The light receiver fiber 121B may also be processed in a well known fashion such that some of the light emitted from the emitting fiber 121A and passing through the fluid responsive medium 122 is caught in the receiving fiber end 121B and transmitted via the fiber optic cable 114 and across the connector 115 back to the light sensor 142.

Figure 4:
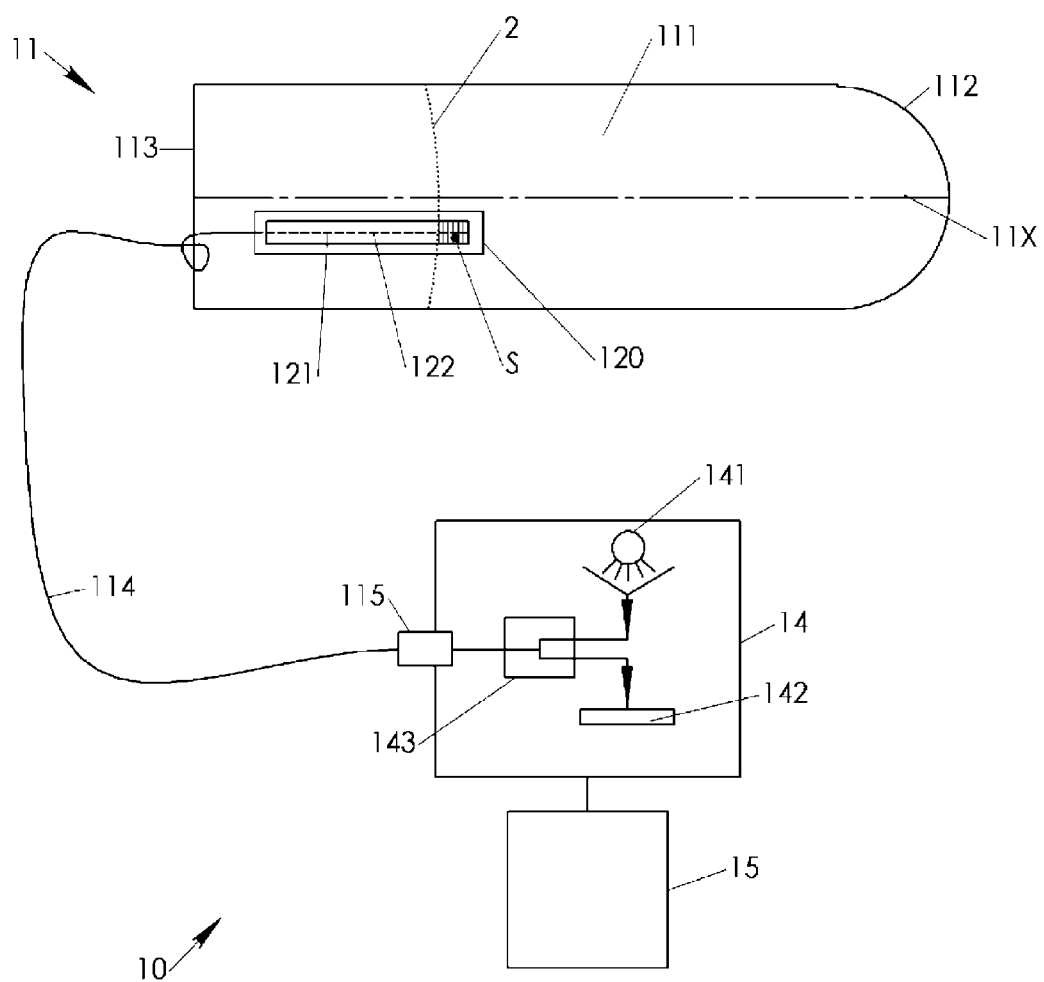
FIG. 4 is a schematic view of a fourth embodiment of the invention.

According to FIG. 4, light emitter 121A and light receiver 121B may be combined in conjunction with a well known optic gate 143 in the processor 14. The optic gate 143 redirects the returning light beam towards the light sensor 142 while switching through the light from the light source 141 towards the saturation sensor 120. In such a single signal terminal 121 configuration, the fluid responsive medium 122 may be reflectively optically responsive such that light emitted from the single signal terminal 121 is back reflected while attenuated and/or spectral changed. The reflection may be diffuse in case of a conventional gauze material utilized as the fluid responsive medium 122. As a favorable result, the single fiber saturation sensor 120 is highly consistent in its wetting response signal S strength since there are no spacing fluctuations between emitter and receiver that eventually reduce signal precision and repeatability.

The notifier 15 may be an acoustic notifier such as a buzzer. Acoustic notification may vary in tone, loudness, and/or time interval to provide a distinguishable information to the user about the tampon's 11 saturation boundary 2 progress. The notifier 15 may also be a tactile notifier such as a vibrating element configured for skin transmitted vibration notification. The notifier 15 may be structurally separated from the processor 14 and in wireless communication with the processor 14 via a second signal line 119 (FIG. 1). In that way, the processor may be carried conveniently attached to undergarment in proximity to the tampon 11 whereas the notifier 15 may be positioned at a location suitable for communication to and/or with the tampon 11 wearer.

The notifier 15 may be a software application installed on a portable multifunction device such as but not limited to a cellular phone or a handheld computing device. At the time of this invention, portable multifunction devices include features such as wireless communication capabilities well known under the term Bluetooth™ that are suitable for communicating with peripheral devices such as the processor 14. Upon installation of the notifier 15 software, the portable multifunction device may provide, visual, acoustic or other well known notification via its built in hardware features.

Figure 7:
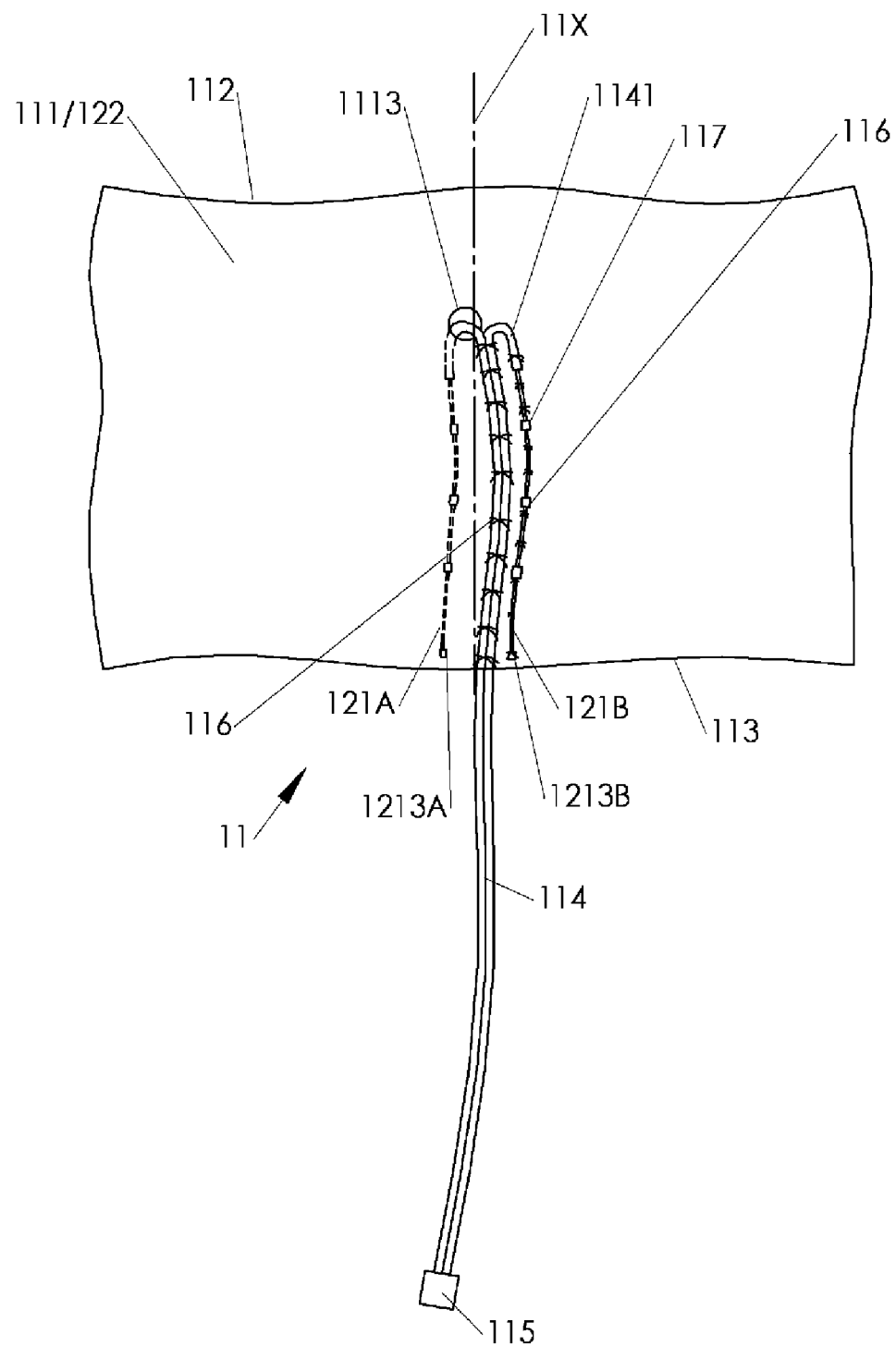
FIG. 7 is a schematic view of a fifth embodiment of the present invention at an intermediate fabrication stage.

Referring to FIG. 7, an embodiment of the invention features the fluid responsive medium 122 as integral part of the fluid absorption body 111, which may be of a gauze material coiled into a cylindrical shape. In FIG. 7, an intermediate fabrication stage of the tampon 11 is schematically depicted at which the gauze material 111/122 may be still in uncoiled condition. The first signal line 114 in the preferred configuration of a cable may be sewed on the gauze material 111/122 via seams 16 such that operational tampon 11 may be pulled out of the vaginally inserted position 1 via the cable 114. Sewing may be particularly suitable since it provides for an axially straight integration of the cable 114 inside the fluid absorption body 111, which assists the coiling of the gauze material 111/122 around saturation progress axis 11X as may be well appreciated by anyone skilled in the art. Optionally, the backwards bending signal terminal(s) 121A, 121B may also be sewn on to the gauze material 111/122.

Separation and spacing between signal terminals 121A, 121B may be provided by the gauze material 111/122. This may be accomplished by having one signal terminal 121 backwards through an optional hole 1113 in the gauze material 111/122. The signal terminal 121A is depicted in FIG. 7 in dashed lines to indicate it being on the backside of the gauze material 111/122.

At least one but preferably all proximal signal terminals 121A, 121B are preferably an integral part of the cable 114 and backwards and extending from the sewn on portion of the cable 114 such that the signal terminal ends 1213A, 1213B are in immediate proximity to the peripheral end 113. As a favorable result, the progress of the blood saturation boundary 2 may be monitored closest to the peripheral end 113 such that a user of the tampon saturation monitoring system 10 may be notified with highest precision until the very moment the tampon 11 reaches its fluid absorption limit. The cable signal terminals 121A, 121B may be composed of thin wire strands held together by the spacers 117.

Figure 8:
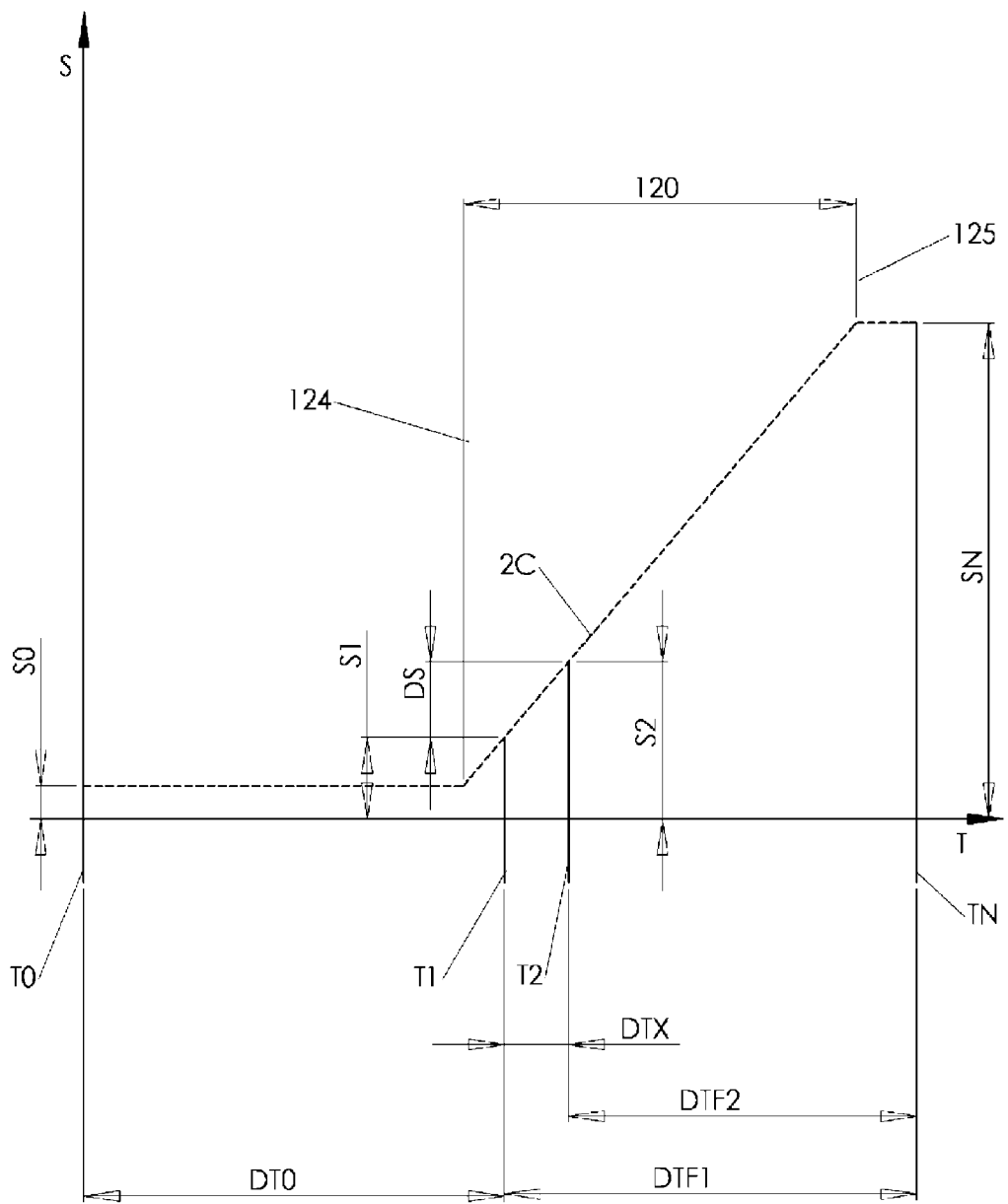
FIG. 8 is a representative diagram of blood saturation progress in a tampon and correlated saturation signals and signal timing.

The signal processor 14 may be a simple micro controller. Its circuitry may be configured and/or programmed to reset during disconnection or connection of a connector 115 indicating a tampon 11 change. Referring to FIG. 8 and upon connection of the connector 115 with the processor 14 at T0, the saturation sensor 120 may be tested as is well known in the art. A calibration signal S0 may be received from the processor 14 during initial testing. The moment T0 of initial connection may be recorded by the processor 14 as well as a second moment T1 of the initial receipt of the wetting response signal S1. Second moment T1 occurs when the saturation boundary 2 has progressed so far as to reach the frontal end of the saturation sensor 120. In the case of a saturation sensor 120 configuration that provides a gradual and proportional wetting response signal S as described above, the wetting response signal S may increase in amplitude as the saturation boundary 2 progresses axially along the saturation sensor 120. This is reflected in the graph of FIG. 8 by the inclining portion of the curve 2C within the boundaries of the saturation sensor 120.

The processor 14 may time an initial signal delay DTO between the first moment T0 and second moment T1. In case of an estimated progression behavior of the saturation boundary 2 as depicted by the curve 2C in FIG. 8, the processor 14 may process the tampon 11 full forecast DTF1 from the initial signal delay DTO and from an initial amplitude of the wetting response signal S1. Any wetting response signals at and below the testing amplitude S0 may be disregarded by the processor 14 and signal processing may initiate with the initial measurement at T1 at which the signal amplitude is above the testing signal S0 amplitude.

Additional measurements may be performed by the processor 14 in time intervals DTX and the tampon 11 full forecast DTF2 may be computationally updated. Signal amplitude of the wetting response signal S2 may be in a difference DS to the initial wetting response signal S1 in case of a saturation sensor 120 with gradually and proportional wetting response signal as described above.

The more measurements that are performed the more accurate the tampon 11 full forecast DTF1, or DTF2 may be computed and the error margin for the tampon 11 full moment TN brought to a minimum. A user of the tampon saturation monitoring system 10 can monitor the saturation progress of the tampon 11 with a precision that increases as the tampon 11 reaches its fluid absorption limit at which the wetting response signal SN may have a maximum amplitude.

The interval measurements T1, T2, TN provide for a minimum battery consumption and consequently a miniature configuration of the processor 14. The battery life of the processor 14 may correspond to a predetermined time of use of a number of tampons 11 packaged together with the processor 14 in a set.

After vaginally inserting the tampon 11, the connector 115 may be connected with the processor 14 and the saturation sensor 120 may be initially tested and the connection moment T0 eventually recorded. The processor 14 may be activated but its signal processing remains dormant until an initial measurement T1 with an initial signal amplitude S1 that exceeds test signal amplitude S0 is recognized by the processor 14. At the moment T1, the processor's 14 computing capacity may be activated and a notification initially passed on to the user via the notifier 15. The user's attention is brought to an upcoming tampon 11 change and the user can conveniently plan ahead to timely change the tampon 11 without worrying of missing the tampon's 11 fluid absorption limit.

Accordingly the scope of the present invention described in the figures and the specification above is set forth by the following claims and their legal equivalent:

What is claimed is:

1. A tampon saturation monitoring system comprising:
   a. a tampon including:
      i. a fluid absorption body protruding along a saturation progress axis, said fluid absorption body including a fluid access end and a peripheral end opposite to said fluid access end in the direction of said saturation progress axis;
      ii. a saturation sensor extending axially with respect to said saturation progress axis in between said fluid access end and said peripheral end, said saturation sensor including at least two proximal signal terminals having a signal potential across a fluid responsive medium that is separating said at least two proximal signal terminals, said fluid responsive medium being in a wetting communication with said fluid absorption body, said fluid saturation sensor generating a gradual wetting response signal in conjunction with an axially progressing saturation boundary of said body fluid absorption element;
      iii. a first signal line peripherally connecting said saturation sensor across said peripheral end;
   b. a signal processor in a first communication with said saturation sensor via said first signal line, said signal processor monitoring the progress of said saturation boundary based on the wetting response signal; and
   c. a notifier in communication with said signal processor, said notifier providing notification about said saturation boundary progress in response to a signal from said signal processor.

2. The tampon saturation monitoring system of claim 1, wherein at least one of said processor and said notifier provides a tampon full forecast from said gradual wetting response signal.

3. A tampon saturation monitoring system including a tampon comprising:
   a. a fluid absorption body protruding along a saturation progress axis, said fluid absorption body including a fluid access end and a peripheral end opposite to said fluid access end in the direction of said saturation progress axis;
   b. a saturation sensor positioned in between said fluid access end and said peripheral end, said saturation sensor including at least two proximal signal terminals having a signal potential across a fluid responsive medium that is separating said at least two proximal signal terminals, said fluid responsive medium being in a wetting communication with said fluid absorption body, said fluid saturation sensor generating a wetting response signal in conjunction with an axially progressing saturation boundary of said body fluid absorption element; and
   c. a first signal line peripherally connecting said saturation sensor across said peripheral end, wherein said first signal line is a cable.

4. A tampon saturation monitoring system, including a tampon comprising:

a. a fluid absorption body protruding along a saturation progress axis, said fluid absorption body including a fluid access end and a peripheral end opposite to said fluid access end in the direction of said saturation progress axis;

b. a saturation sensor positioned in between said fluid access end and said peripheral end, said saturation sensor including at least two proximal signal terminals having a signal potential across a fluid responsive medium that is separating said at least two proximal signal terminals, said fluid responsive medium being in a wetting communication with said fluid absorption body, said fluid saturation sensor generating a wetting response signal in conjunction with an axially progressing saturation boundary of said body fluid absorption element;

c. a cable peripherally connecting said saturation sensor across said peripheral end; and wherein said cable is structurally combined with said fluid absorption body via a knot at said peripheral end such that said tampon may be pulled out of a vaginally arrested position of said tampon via said cable.

5. A tampon saturation monitoring system, including a tampon comprising:

a. a fluid absorption body protruding along a saturation progress axis, said fluid absorption body including a fluid access end and a peripheral end opposite to said fluid access end in the direction of said saturation progress axis;

b. a saturation sensor positioned in between said fluid access end and said peripheral end, said saturation sensor including at least two proximal signal terminals having a signal potential across a fluid responsive medium that is separating said at least two proximal signal terminals, said fluid responsive medium being in a wetting communication with said fluid absorption body, said fluid saturation sensor generating a wetting response signal in conjunction with an axially progressing saturation boundary of said body fluid absorption element;

c. a cable peripherally connecting said saturation sensor across said peripheral end; and wherein at least one of said at least two proximal signal terminals is an integral part of a strand of said cable.

6. A tampon saturation monitoring system, including a tampon comprising:

a. a fluid absorption body protruding along a saturation progress axis, said fluid absorption body including a fluid access end and a peripheral end opposite to said fluid access end in the direction of said saturation progress axis;

b. a saturation sensor positioned in between said fluid access end and said peripheral end, said saturation sensor including at least two proximal signal terminals having a signal potential across a fluid responsive medium that is separating said at least two proximal signal terminals, said fluid responsive medium being in a wetting communication with said fluid absorption body, said fluid saturation sensor generating a wetting response signal in conjunction with an axially progressing saturation boundary of said body fluid absorption element;

c. a cable peripherally connecting said saturation sensor across said peripheral end; and wherein at least one of said at least two proximal signal terminals is a strand of said cable separated and spaced from at least one other of said at least two proximal signal terminals by a number of spacers axially arrayed with respect to said saturation progress axis.

7. The tampon saturation monitoring system of claim 6, wherein said cable includes a surrounding insulation, and wherein at least one of said number of axially arrayed spacers is of said surrounding insulation.

8. A tampon saturation monitoring system, including a tampon comprising:

a. a fluid absorption body protruding along a saturation progress axis, said fluid absorption body including a fluid access end and a peripheral end opposite to said fluid access end in the direction of said saturation progress axis;

b. a saturation sensor extending axially with respect to said saturation progress axis in between said fluid access end and said peripheral end, said saturation sensor including at least two proximal signal terminals having a signal potential across a fluid responsive medium that is separating said at least two proximal signal terminals, said fluid responsive medium being in a wetting communication with said fluid absorption body, said fluid saturation sensor generating a gradual wetting response signal in conjunction with an axially progressing saturation boundary of said body fluid absorption element;

wherein:

a. said at least two proximal signal terminals are electric conductors;

b. a physical property change due to a menstrual blood wetting of said fluid responsive medium is a gradual electric resistance change; and c. said gradual wetting response signal is a resistive signal occurring in between said electric conductors and across said fluid responsive medium in conjunction with said gradual electric resistance change and a voltage difference between said two electric conductors.

9. The tampon saturation monitoring system of claim 8, wherein one of said electric conductors is an enveloping conductor, and wherein said enveloping conductors is an electric ground.

10. The tampon saturation monitoring system of claim 9, wherein said enveloping conductor is fluid permeable.

11. The tampon saturation monitoring system of claim 10, wherein said first signal line is a coaxial cable, and wherein said enveloping conductor is an integral conductive part of a shielding mesh of said coaxial cable.

12. The tampon saturation monitoring system of claim 8, wherein said voltage difference is a fraction of a processing voltage of said processor selected in conjunction with:

a. a predetermined maximum conductivity between at least one of said proximal signal terminals and a proximal vaginal lining; and b. a maximum allowed body leakage current.

13. A tampon saturation monitoring system, including a tampon comprising:

a. a fluid absorption body protruding along a saturation progress axis, said fluid absorption body including a fluid access end and a peripheral end opposite to said fluid access end in the direction of said saturation progress axis;

b. a saturation sensor positioned in between said fluid access end and said peripheral end, said saturation sensor including at least two proximal signal terminals having a signal potential across a fluid responsive medium that is separating said at least two proximal signal terminals;

wherein said fluid responsive medium is integral part of said fluid absorption body; and wherein said fluid saturation sensor generating a wetting response signal in conjunction with an axially progressing saturation boundary of said body fluid absorption element.

14. The tampon saturation monitoring system of claim 13, wherein:
   a. said fluid absorption body is of gauze material; and
   b. said at least two proximal signal terminals being part of a cable sewed on said gauze material; and
      wherein said cable is peripherally connecting said saturation sensor across said peripheral end such that said tampon may be pulled out of a vaginally arrested position of said tampon via said cable.

15. The tampon saturation monitoring system of claim 14, wherein at least one of said at least two proximal signal terminals is backwards bending extending from a sewed on portion of said cable such that a signal terminal end is in immediate proximity to said peripheral end.

16. The tampon saturation monitoring system of claim 15, wherein said backwards bending signal terminal is sewed on to said gauze material.

17. The tampon saturation monitoring system of claim 15, wherein one of said backwards bending signal terminal is said bent backwards through said gauze material such that said one of said backwards bending signal terminal is separated and spaced apart from one other of said backwards bending signal terminal by said gauze material.

18. A tampon system comprising:
   a. a tampon formed from an absorbent material and having distal and proximal ends with said tampon being insertable into a vagina from said distal end thereof;
   b. a pair of wires, with one set of ends thereof being positioned within said tampon near said proximal end thereof and with said opposed ends of said pair of wires being terminated in a first electrical connector located outside of said tampon, wherein said pair of wires are spaced apart within said absorbent material and are defining in conjunction with said absorbent material a saturation sensor;
   c. a monitor having a second electrical connector, said monitor measuring an electric resistance between said pair of wires in conjunction with a blood saturation boundary progressing along said pair of wires spaced apart within said absorbent material and generating a wetness signal while said second electrical connector being connected with said first electrical connector; and
   d. a notifier housed together with said monitor and in response to receipt of said wetness signal generating a user perceptible alert signal.

19. A tampon comprising:
   a. a fluid absorption body protruding along a saturation progress axis, said fluid absorption body including a fluid access end and a peripheral end opposite to said fluid access end in the direction of said saturation progress axis;
   b. a saturation sensor positioned in between said fluid access end and said peripheral end, said saturation sensor including at least two proximal signal terminals and a portion of said fluid absorption body that is in between said proximal signal terminals, said proximal signal terminals having a signal potential across said portion of said fluid absorption body, said fluid saturation sensor generating a wetting response signal in conjunction with a progressing saturation boundary of said body fluid absorption body; and
   c. a first signal line peripherally connecting said saturation sensor across said peripheral end.

20. The tampon of claim 19, wherein said at least two proximal signal terminals are integral part of said first signal line.

* * * * *